United States Patent [19]
Scalice et al.

[11] Patent Number: 5,587,287
[45] Date of Patent: Dec. 24, 1996

[54] THERMOSTABLE POLYMERASE SPECIFIC ANTIBODY-CONTAINING DNA AMPLIFICATION COMPOSITION AND KIT

[75] Inventors: Edward R. Scalice; David J. Sharkey, both of Rochester; Kenneth G. Christy, Jr., North Chili; Theodore W. Esders, Webster; John L. Daiss, Rochester, all of N.Y.

[73] Assignee: Johnson & Johnson Clinical Diagnostics, Inc., Rochester, N.Y.

[21] Appl. No.: 224,218

[22] Filed: Apr. 7, 1994

Related U.S. Application Data

[62] Division of Ser. No. 958,144, Oct. 7, 1992, Pat. No. 5,338,671.

[51] Int. Cl.⁶ ............... C12Q 1/68; C12Q 1/70; C12P 19/34; C07K 16/40
[52] U.S. Cl. ............... 435/6; 435/91.2; 435/5; 530/388.26; 530/350
[58] Field of Search ............... 530/350, 388.26; 435/91.2, 6, 5

[56] References Cited

U.S. PATENT DOCUMENTS

| | | | |
|---|---|---|---|
| 4,042,862 | 8/1977 | Spector | 424/95 |
| 4,638,028 | 1/1987 | Lui et al. | 524/387 |
| 4,889,818 | 12/1989 | Gelfand et al. | 435/194 |
| 4,965,188 | 10/1990 | Mullis et al. | 435/6 |
| 5,210,036 | 5/1993 | Comb et al. | 435/194 |

FOREIGN PATENT DOCUMENTS

89/06691  7/1989  WIPO.

OTHER PUBLICATIONS

Stratagene Catalog (1988) p. 39.
Harlow, E & D. Lane, Antibodies in Laboratory Manual (1988) pp. 27, 141, 142, 231, 236, 237.
Bobrovnik, S. A. et al. Dynamics and Mechanism of Antibody Thermoinactivation Biopolim. Kletka (1988) 4:310–313.

*Primary Examiner*—Stephanie W. Zitomer
*Assistant Examiner*—Dianne Rees

[57] ABSTRACT

Antibodies which are specific to a thermostable DNA polymerase can be used to reduce or eliminate the formation of non-specific products in polymerase chain reaction methods. These antibodies and other temperature sensitive inhibitors are effective to inhibit DNA polymerase enzymatic activity at a certain temperature $T_1$ which is generally below about 85° C. The inhibitors are irreversibly inactivated at temperature $T_2$ which is generally above about 40° C. $T_2$ is also greater than $T_1$. Such inhibitors can be supplied individually or in admixture with the DNA polymerase in a diagnostic test kit suitable for PCR.

18 Claims, 1 Drawing Sheet

THERMOSTABLE POLYMERASE SPECIFIC ANTIBODY-CONTAINING DNA AMPLIFICATION COMPOSITION AND KIT

This application is a divisional of application Ser. No. 08/958,144, filed Oct. 7, 1992, now U.S. Pat. No. 5,338,671 issued Aug. 16, 1994.

FIELD OF THE INVENTION

This invention relates to a composition comprising a DNA polymerase and a DNA polymerase inhibitor which is temperature sensitive. It also relates to diagnostic test kits and to methods of amplification using the composition. In general, this invention relates to PCR and its use for diagnostics.

BACKGROUND OF THE INVENTION

Technology to detect minute quantities of nucleic acids has advanced rapidly over the last two decades including the development of highly sophisticated hybridization assays using probes in amplification techniques such as PCR. Researchers have readily recognized the value of such technology to detect diseases and genetic features in human or animal test specimens. The use of probes and primers in such technology is based upon the concept of complementarity, that is the bonding of two strands of a nucleic acid by hydrogen bonds between complementary nucleotides (also known as nucleotide pairs).

PCR is a significant advance in the art to allow detection of very small concentrations of a targeted nucleic acid. The details of PCR are described, for example, in U.S. Pat. No. 4,683,195 (Mullis et al), U.S. Pat. No. 4,683,202 (Mullis) and U.S. Pat. No. 4,965,188 (Mullis et al), although there is a rapidly expanding volume of literature in this field. Without going into extensive detail, PCR involves hybridizing primers to the strands of a targeted nucleic acid (considered "templates") in the presence of a polymerization agent (such as a DNA polymerase) and deoxyribonucleoside triphosphates under the appropriate conditions. The result is the formation of primer extension products along the templates, the products having added thereto nucleotides which are complementary to the templates.

Once the primer extension products are denatured, one copy of the templates has been prepared, and the cycle of priming, extending and denaturation can be carried out as many times as desired to provide an exponential increase in the amount of nucleic acid which has the same sequence as the target nucleic acid. In effect, the target nucleic acid is duplicated (or "amplified") many times so that it is more easily detected. Despite the broad and rapid use of PCR in a variety of biological and diagnostic fields, there are still practical limitations which must be overcome to achieve the optimum success of the technology. PCR also produces considerable inefficiency in the use of expensive reagents.

Many amplification procedures yield nonspecific side products of nucleic acids that are not targeted. Sometimes nonspecificity is caused by mispriming by the primers whereby they anneal to non-targeted nucleic acids. Many PCR procedures also yield primer dimers or oligomers and double-stranded side products containing the sequences of several primer molecules joined end-to-end. All of these unwanted products adversely affect accurate and sensitive detection of the target nucleic acid.

The problem caused by unwanted side products is particularly acute when the target nucleic acid is present in very low concentrations, for example, less than about 1000 molecules. Such low numbers of molecules can arise from early stages of infectious diseases or because of a very small specimen, such as may be the situation with forensic investigations.

The high sensitivity of PCR makes the process especially susceptible to contamination where amplified target nucleic acid from one reaction is transferred into subsequent reactions using the same primers, generating a false positive in the later reactions.

Under ideal conditions for PCR, the primers used will bind very specifically to the target nucleic acid only, particularly at elevated temperatures used in the process. However, the reaction mixture may also be held at lower temperatures at certain times (for example during manufacture, shipping or before use by a customer), and the primers may undesirably bind to the non-targeted nucleic acids. If this occurs, nonspecific primer extension products and primer dimers can form which can be amplified along with the target nucleic acid during PCR cycles at elevated temperatures. These undesired products can obscure any amplified target nucleic acid (that is, produce high background). The primers are less efficient in amplification of the target nucleic acid, and thus the process requires more of the highly expensive reagents to produce an accurate result. Because reagents in the reaction are utilized to make nonspecific products, less specific product is produced, rendering the process less sensitive for target nucleic acid.

Extensive work has been carried out to isolate and characterize DNA polymerases from many sources and for many potential uses. Antibodies to some of such polymerases have also been developed (see for example, U.S. Pat. No. 4,638,028 of Lui et al) for diagnostic tests and other potential industrial and medical uses.

Thermostable DNA polymerases have also been described, for example in WO-A-89/06691 (Cetus). These DNA polymerases have found advantageous use in PCR because of their stability at high temperatures used in certain PCR steps. Accordingly, almost everyone uses thermostable DNA polymerases when carrying out PCR. However, as noted above, the highly powerful nature of PCR has inherent problems, that is, the amplification of nonspecific nucleic acids and the formation of primer dimers. These problems are particularly acute in the presence of thermostable DNA polymerases which have some activity even at relatively lower temperatures (that is, below about 50° C.).

It would be desirable to reduce or eliminate the formation of nonspecific products and primer dimers in PCR, especially with the use of thermostable DNA polymerases.

This problem has been met in one fashion as described in copending U.S. Ser. No. 880,911 (filed May 7, 1992 by Yoo, Sharkey, Christy, Jr. and Esders) by encapsulating one or more of the reagents used in PCR. The encapsulating materials are designed to melt at the temperatures normally used for PCR so the reagents are released for reaction only at the proper time.

Our colleagues have found this invention to be very useful, but there is a need for further improvement. In particular, the use of encapsulating materials can be tedious and expensive, especially in large quantities, and some PCR reagents are encapsulated only with considerable difficulty. Thus, there is a need to overcome the problems of the art without the use of encapsulation.

SUMMARY OF THE INVENTION

The problems noted above have been solved with a composition comprising a thermostable DNA polymerase, and a temperature sensitive inhibitor for the DNA polymerase, the inhibitor being capable of inhibiting the DNA polymerase at a temperature $T_1$ which is less than about 85° C. such that the enzymatic activity of the DNA polymerase is inhibited, and the inhibitor being irreversibly inactivated at a temperature $T_2$ which is greater than $T_1$ and is also greater than about 40° C., so that the DNA polymerase regains its enzymatic activity.

This invention also provides a kit for polymerase chain reaction comprising, in separate packaging:

a. the composition described above, and b. at least one additional PCR reagent.

Another kit of this invention comprises, in separate packaging:

a. a thermostable DNA polymerase, and b. a temperature sensitive DNA inhibitor for the polymerase, the inhibitor being capable of inhibiting the DNA polymerase at a temperature $T_1$ which is less than about 85° C. such that the enzymatic activity of the DNA polymerase is inhibited, and the inhibitor being irreversibly inactivated at a temperature $T_2$ which is greater than $T_1$ and is also greater than about 40° C., so that the DNA polymerase regains its enzymatic activity.

Moreover, a method for the amplification of a target nucleic acid comprises the steps of:

A. contacting a specimen suspected of containing a target nucleic acid with the following polymerase chain reaction reagents:

1) a primer complementary to said target nucleic acid,
2) a thermostable DNA polymerase,
3) a temperature sensitive inhibitor for the thermostable DNA polymerase, the inhibitor being capable of inhibiting the DNA polymerase at a temperature $T_1$ which is less than about 85° C. such that the enzymatic activity of the DNA polymerase is inhibited, and the inhibitor being irreversibly inactivated at a temperature $T_2$ which is greater than $T_1$ and is also greater than about 40° C., so that the DNA polymerase regains its enzymatic activity, 4) a DNA polymerase cofactor, and
5) a deoxyribonucleoside-5'-triphosphate, and B. bringing the resulting mixture to at least temperature $T_2$ to irreversibly inactivate the DNA polymerase inhibitor and allowing the formation of primer extension products.

A monoclonal antibody which is specific to a thermostable DNA polymerase is also provided by this invention. This antibody:

a) has an association constant of at least about $1 \times 10^7$ molar$^{-1}$ with the DNA polymerase, b) is capable of inhibiting the DNA polymerase at a temperature $T_1$ which is less than about 85° C. such that the enzymatic activity of the DNA polymerase is inhibited, the antibody being irreversibly inactivated at a temperature $T_2$ which is greater than $T_1$ and is also greater than about 40° C., so that the DNA polymerase regains its enzymatic activity, and c) is of either the IgM or IgG class.

The present invention overcomes the problem of amplification of non-target nucleic acids by inactivating the DNA polymerase used in PCR until reaction is desired. The formation of primer dimers is also greatly reduced. Moreover, the disadvantages of the use of encapsulated PCR reagents (albeit an advance over prior art methods) are avoided.

These advantages are achieved by mixing a thermostable DNA polymerase with a temperature sensitive inhibitor for the DNA polymerase. This inhibitor inactivates the polymerase (that is, it causes the polymerase to lose its enzymatic activity) at a temperature $T_1$ which is less than about 85° C., but itself becomes irreversibly ineffective for polymerase inactivation at a second temperature $T_2$ which is both greater than $T_1$ and greater than about 40° C. In other words, above $T_2$, the inhibitor irreversibly loses its ability to inhibit the DNA polymerase, and the DNA polymerase regains its enzymatic activity. The inhibitor is deactivated at that higher temperature.

Thus, for a given inhibitor, one can control PCR by keeping the temperature of the DNA polymerase at or below $T_1$, and then let the reaction proceed by raising the temperature of the reaction mix to at least $T_2$. This is a very effective and convenient PCR control means.

BRIEF DESCRIPTION OF THE DRAWINGS

The FIGURE is a photographic image of electrophoretic gel results which are described in more detail in Example 2 below.

DETAILED DESCRIPTION OF THE INVENTION

Figure 1:
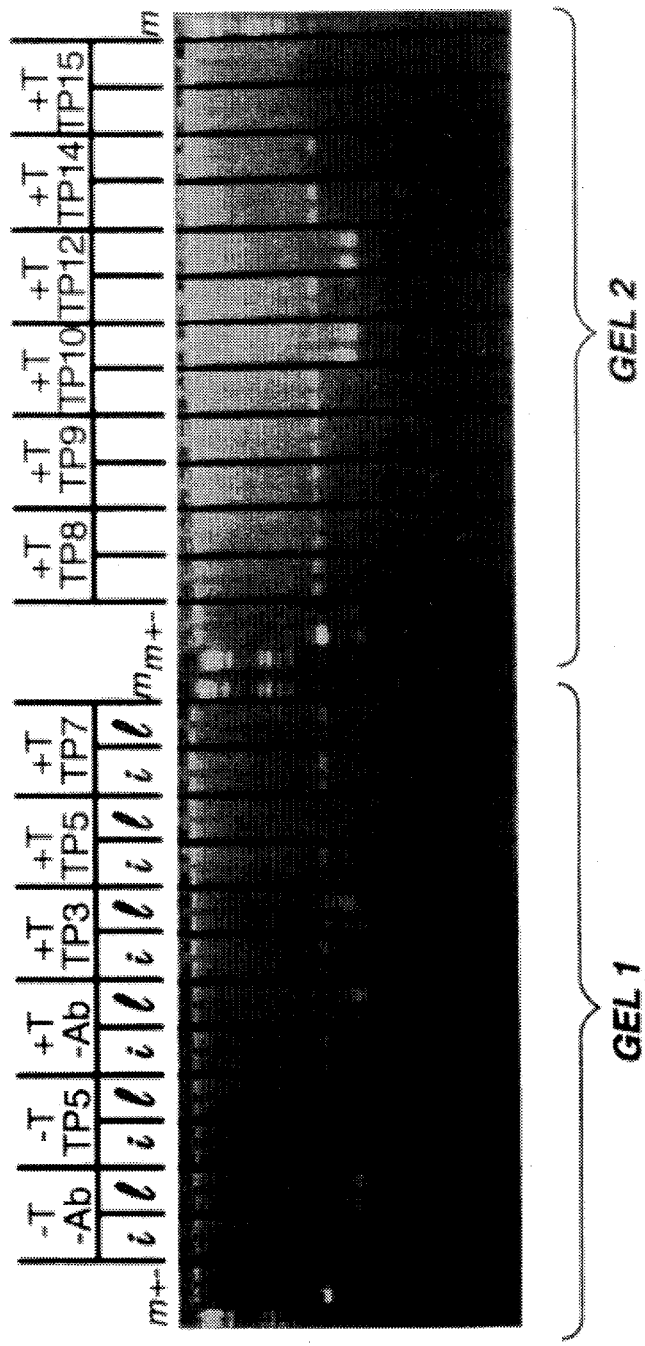

The general principles and conditions for amplification and detection of nucleic acids using polymerase chain reaction are quite well known, the details of which are provided in numerous references including U.S. Pat. No. 4,683,195, U.S. Pat. No. 4,683,202, U.S. Pat. No. 4,965,188 and WO-A-91/12342 and by Guatelli et al, *Clin. Microbiol. Rev.*, 2 (2), pp. 217–226 (1989). In view of the teaching in the art and the specific teaching provided herein, a worker skilled in the art should have no difficulty in practicing the present invention by making the adjustments taught herein to accomplish amplification of a target nucleic acid with reduced amplification of non-targeted nucleic acids.

The present invention is directed to the amplification or detection of one or more specific nucleic acid sequences present in one or more target nucleic acids in a test specimen. Such specimens can include cellular or viral material, hair, body fluids or other materials containing genetic DNA or RNA which can be detected. While the primary purpose of detection is diagnostic in nature, the invention can also be used to improve the efficiency of cloning DNA or messenger RNA, or for obtaining large amounts of the desired sequence from a mixture of nucleic acids resulting from chemical synthesis.

The present invention is especially useful for producing, in exponential quantities relative to the number of reaction steps involved, at least one specific nucleic acid sequence associated with an infectious agent. The product will be a discrete nucleic acid duplex with termini corresponding to the ends of the specific primers employed. Any source of nucleic acid, purified or not, can be utilized as the starting material if it is known to or suspected of containing the specific nucleic acid sequence targeted for detection. Moreover, a plurality of target nucleic acids can be amplified and detected simultaneously by using a corresponding set of primers and detection means for each specific nucleic acid.

Multiple sequences in the same nucleic acid can also be amplified and detected.

Nucleic acids to be detected can be obtained from various sources including plasmids and naturally occurring DNA or RNA from any source (such as bacteria, yeast, viruses, plants and higher animals, humans). It may be extracted from various tissues including blood, peripheral blood mononuclear cells (PBMC), tissue material or other sources known in the art using known procedures. The present invention is particularly useful for the amplification and detection of nucleic acid sequences found in genomic DNA, bacterial DNA, fungal DNA, viral RNA, or DNA or RNA found in bacterial or virus-infected cells.

The method described herein can be used to provide the detection or characterization of specific nucleic acid sequences associated with infectious diseases, genetic disorders or cellular disorders such as cancers. It may also be used in forensic investigations and DNA typing. For purposes of this invention, genetic diseases include specific deletions or mutations in genomic DNA from any organism, such as sickle cell anemia, cystic fibrosis, α-thalassemia, β-thalessemia and others readily apparent to one skilled in the art. Bacteria which can be detected include, but are not limited to, bacteria found in human blood, Salmonella species, Streptococcus species, Chlamydia species, Gonococcal species, *Mycobacterium tuberculosis, Mycobacterium avium* complex, *Legionella pneumophila, Clostridium difficile, Borreglia burgdorferei, Pneumocystis carinii, Mycoplasma Haemophilus influenzae*, Shigella species and Listeria species. Viruses which are detectable include, but are not limited to, herpes, Epstein Barr virus, influenza viruses, cytomegalovirus, human papilloma virus, hepatitis and retroviruses such as HTLV-I, HIV-I and HIV-II. Protozoan parasites, yeasts and molds are also detectable. Other detectable species would be readily apparent to one skilled in the art. The invention is particularly useful for the detection of the presence of DNA associated with various bacteria or viruses, with the amplification and detection of viral DNA being of most interest. Detection of DNA associated with HIV-I (and other retroviruses), cytomegalovirus or human papilloma virus is advantageously accomplished with this invention. Most preferably, it is used to detect DNA associated with retroviruses, such as HIV-I.

As used herein in referring to primers, probes or oligomer fragments to be detected, the term "oligonucleotide" refers to a molecule comprised of two or more deoxyribonucleotides or ribonucleotides, and preferably more than three. Its exact size is not critical but depends upon many factors including the ultimate use or function of the oligonucleotide. The oligonucleotide may be derived by any method known in the art.

A "PCR reagent" refers to any of the reagents considered essential to PCR, namely one or more primers for the target nucleic acid, a thermostable DNA polymerase, a DNA polymerase cofactor, and one or more deoxyribonucleoside-5'-triphosphates.

The term "primer" refers to an oligonucleotide, whether naturally occurring or synthetically produced, which is capable of acting as a point of initiation of synthesis when placed under conditions in which synthesis of a primer extension product complementary to a nucleic acid strand (that is, template) is induced. Such conditions include the presence of nucleotides (such as the four standard deoxyribonucleoside-5'-triphosphates), a thermostable DNA polymerase, and suitable temperature, pH and cofactor.

The primer is preferably single stranded for maximum efficiency in amplification, but can contain a double stranded region if desired. It must be long enough to prime the synthesis of extension products in the presence of the DNA polymerase. The exact size of each primer will vary depending upon the use contemplated, the complexity of the targeted sequence, reaction temperature and the source of the primer. Generally, the primers used in this invention will have from 12 to 60 nucleotides, and preferably, they have from 18 to 45 nucleotides.

The primers used in the present invention are selected to be "substantially complementary" to the different strands of each specific sequence to be amplified. This means that they must be sufficiently complementary to hybridize with their respective strands to form the desired hybridized products and then be extendable by a DNA polymerase. In the preferred and most practical situation, the primer has exact complementarity to the target nucleic acid.

In some situations where mismatches between the targeted nucleic acid and a primer are suspected, the effect of the mismatch may be overcome using specialized primer compositions, such as those described for example in EP-A-0 393 743 (published Oct. 24, 1990) and EP-A-0 417 842 (published Mar. 20, 1991).

Primers useful herein can be obtained from a number of sources or prepared using known techniques and equipment, including for example, an ABI DNA Synthesizer (available from Applied Biosystems) or a Biosearch 8600 Series or 8800 Series Synthesizer (available from Milligen-Biosearch, Inc.) and known methods for their use (for example as described in U.S. Pat. No. 4,965,188). Naturally occurring primers isolated from biological sources are also useful (such as restriction endonuclease digests). As used herein, the term "primer" also refers to a mixture of primers.

As used herein, a "probe" is an oligonucleotide which is substantially complementary to a nucleic acid sequence of the target nucleic acid and which are generally not allowed to form primer extension products. The probes can be of any suitable length of nucleotides, but generally, they have from about 12 to about 40 nucleotides. They can be labeled (commonly at the 3' end) with any suitable detectable material, as described below. They can also be attached to a water-insoluble substrate of some type for capture of the targeted nucleic acid using known technology.

A thermostable DNA polymerase is an enzyme which will add deoxynucleoside monophosphate molecules to the 3' hydroxy end of the primer in a complex of primer and template, but this addition is in a template dependent manner (that is, dependent upon the specific nucleotides in the template).

The DNA polymerase is "thermostable" meaning that it is stable to heat and preferentially active at higher temperatures, especially the high temperatures used for denaturation of DNA strands. More particularly, the thermostable DNA polymerases are not substantially inactivated at the high temperatures used in polymerase chain reactions as described herein. Such temperatures will vary depending upon a number of reaction conditions, including pH, the nucleotide composition of the target nucleic acid and primers, the length of primer, salt concentration and other conditions known in the art and will be in the ranges noted below.

A number of thermostable DNA polymerases have been reported in the art, including those mentioned in detail in U.S. Pat. No. 4,965,188 and U.S. Pat. No. 4,889,818 (Gelfand et al). Particularly useful polymerases are those obtained from various Thermus bacterial species, such as *Thermus aquaticus, Thermus thermophilus, Thermus filifor-* mis or *Thermus flavus*. Other useful thermostable polymerases are obtained from a variety of other microbial sources including *Thermococcus literalis, Pyrococcus furiosus,* Thermotoga sp. and those described in WO-A-89/06691 (published Jul. 27, 1989). Some useful polymerases are commercially available. A number of techniques are known for isolating naturally-occurring polymerases from organisms, and for producing genetically engineered enzymes using recombinant techniques, as noted in the art cited in this paragraph.

A DNA polymerase cofactor refers to a nonprotein compound on which the enzyme depends for activity. Thus, the enzyme is catalytically inactive without the presence of the cofactor. A number of such materials are known cofactors including manganese and magnesium compounds. Such compounds contain the manganese or magnesium in such a form that divalent cations are released into an aqueous solution. Useful cofactors include, but are not limited to, manganese and magnesium salts, such as chlorides, sulfates, acetates and fatty acid salts (for example, butyric, caproic, caprylic, capric and lauric acid salts). The smaller salts, that is chlorides, sulfates and acetates, are preferred.

Magnesium salts, such as magnesium chlorides and sulfates are most preferred in the practice of the invention.

Also needed for PCR is a deoxyribonucleoside-5= triphosphate, such as dATP, dCTP, dGTP, dTTP or dUTP. Analogues such as dITP and 7-deaza-dGTP are also useful. It is conventional to identify dATP, dCTP, dGTP and dTTP collectively as dNTP's.

The thermostable DNA polymerase described above is used in the practice of this invention in combination with a water-soluble temperature sensitive inhibitor. This inhibitor acts to bind to and to inactivate the polymerase at temperature $T_1$ which is generally below about 85° C. For most practical purposes, $T_1$ is below about 55° C.

Advantageously, however, the water-soluble temperature sensitive inhibitor dissociates from the DNA polymerase and becomes ineffective to inactivate the DNA polymerase at temperature $T_2$ which is generally above about 40° C. Preferably, $T_2$ is at least 5° C. above $T_1$. Very useful embodiments of this invention are shown in the examples below, in which $T_1$ is generally from about 40° C. to about 55° C. and $T_2$ is generally from about 75° to about 95° C.

The inhibitor can be any biological or chemical molecule which will complex with the thermostable DNA polymerase to effect the noted temperature-dependent responses in the polymerase. Generally, the combined molecule (or complex) of DNA polymerase and temperature sensitive inhibitor is water-soluble. The inhibitor can be DNA polymerase-binding proteins which bind and release the DNA polymerase in response to temperature. Particularly useful inhibitors are antibodies (monoclonal or polyclonal) specific to the DNA polymerase which have the noted binding and releasing properties. The term "antibodies" includes the biological molecules one skilled in the art would normally understand that term to include, but in addition, it includes genetically prepared equivalents thereof, and chemically or genetically prepared fragments of antibodies (such as Fab fragments). The antibodies (and fragments thereof), can be used singly or in mixtures in the practice of this invention.

Useful antibodies can be prepared using conventional technologies. For example, polyclonal antibodies can be prepared by immunizing a suitable host mammal with a DNA polymerase (naturally occurring or synthetically prepared equivalent, or protein conjugate) with a suitable adjuvant (for example, Freund's complete adjuvant). Booster injections can be given at various intervals to increase titer. Serum samples are generally collected at certain time intervals and tested for DNA polymerase specificity. Desired sera of sufficient titer are generally purified using conventional means such as ion exchange and affinity chromatography (for example, using Protein A or Protein G matrices).

More preferably, monoclonal antibodies can be prepared from the immune cells of DNA polymerase immunized mice or rats using conventional procedures, such as those described by Milstein et al, *Nature*, 256, pp. 495–497 (1975) and hybridoma cell lines, whereby antibody secreting cells of the host animal are isolated from lymphoid tissue (such as the spleen) and fused with mouse myeloma cells (for example, SP2/0-Ag14 murine myeloma cells) in the presence of polyethylene glycol, diluted into selective media and plated in multiwell tissue culture dishes. About 7–14 days later, the hybridoma cells which secrete the desired antibodies are harvested for use or frozen in storage. The culture supernatants can also be tested for the presence of the desired antibodies. To produce sufficient amount of antibody, the hybridoma cells can be grown in static culture, hollow fiber bioreactors or used to produce ascitic tumors in mice. Purification can be carried out similar to that described for polyclonal antibodies.

The monoclonal antibodies generally have an affinity for at least one thermostable DNA polymerase as defined by having an association constant of at least about $1 \times 10^7$ molar$^{-1}$. Preferably, the antibody is of either the IgG or IgM class. Most preferably, it is of the IgG class.

The following list of representative antibodies are useful in the practice of this invention:

TABLE I

| Antibody | Type | Other | Characteristics |
|---|---|---|---|
| TP1 | IgG$_1$ | mouse | monoclonal |
| TP2 | IgG$_1$ | mouse | monoclonal |
| TP3 | IgG$_{2b}$ | mouse | monoclonal |
| TP4 | IgG$_{2a}$ | mouse | monoclonal |
| TP5 | IgG$_{2b}$ | mouse | monoclonal |
| TP6 | IgG$_{2b}$ | mouse | monoclonal |
| TP7 | IgG$_{2a}$ | mouse | monoclonal |
| TP8 | IgG$_{2a}$ | mouse | monoclonal |
| TP9 | IgG$_{2a}$ | mouse | monoclonal |
| TP14 | mixture* | mouse | monoclonal |

*mixture including TP1 through TP9

Determination of isotype of cloned antibody cultures was performed following a standard ELISA protocol using goat anti-mouse isotype specific horseradish peroxidase labeled scoring reagents (Fisher Biotech, Pittsburgh).

Microtiter well plates (LINBRO™ E.I.A. II plus or Nunc MaxiSorp™ F96) were coated with recombinant *Thermus aquaticus* DNA polymerase (50 µl/plate well of 2 µg/ml), incubated at room temperature for 1 hour, contacted with gelatin (1%) and TWEEN™ 20 nonionic surfactant (0.05%) in phosphate buffered saline solution (200 µl/plate well), and stored frozen until needed.

Conventional ELISA was performed for initial screening for antibodies by addition of the hybridoma culture supernatant (50 µl/plate well) followed by incubation at room temperature with constant agitation. All incubations were followed by washing five times with TWEEN™ 20 nonionic surfactant (0.05%) in phosphate buffered saline solution using a TITERTEK™ 120 microtiter plate washer. The detection reagents (50 µl/plate well) included goat anti-mouse IgG horseradish peroxidase conjugate (Biorad, 1:3000 dilution in 1% gelation/phosphate buffered saline solution). A substrate used to produce dye (50 μl/plate well) was ABTS peroxidase substrate (Kirkegaard & Perry Laboratories, Gaithersburg, Md.). Incubation for 15 minutes at room temperature produced a dye signal evaluated at 414 nm using a TITERTEK MULTISKAN™ MCC/340 Mark II plate reader.

The affinity constants of several of these antibodies was determined using an ELISA assay procedure as follows:

Competitive ELISA was performed in a similar manner except that soluble antigen in phosphate buffered saline solution containing gelatin (1%) was first added to the ELISA plate followed by addition of diluted cell culture supernatant (25 μl) such that the final DNA polymerase concentration ranged from $3\times10^7$ molar to $3\times10^{-10}$ molar. For estimation of affinity constants, cell culture supernatants were first titrated by ELISA, then used at the dilution where the absorbance starts to drop to assure that soluble antigen was mixed with a limiting amount of specific antibody. Known concentrations of *Thermus aquaticus*, *Thermus thermophilus* and *Thermus filiformis* were used as soluble inhibitors. Affinity constants were estimated from inhibition curves as the concentration of DNA polymerase which yielded half the maximum absorbance.

The following Table IA shows the affinity constants determined for some of the monoclonal antibodies of Table I.

TABLE IA

| Antibody | *Ka-Polymerase from Thermos aquaticus | *Ka-Polymerase from Thermos thermophilus | *Ka-Polymerase from Thermos filiformis |
|---|---|---|---|
| TP1 | $(6.00E-09)^{-1}$ | — | — |
| TP2 | $(5.00E-09)^{-1}$ | $(3.00E-07)^{-1}$ | — |
| TP3 | $(2.50E-09)^{-1}$ | — | $(2.00E-08)^{-1}$ |
| TP4 | $(1.50E-09)^{-1}$ | $(9.00E-09)^{-1}$ | — |
| TP5 | $(4.00E-09)^{-1}$ | $(2.00E-08)^{-1}$ | — |
| TP6 | $(2.50E-09)^{-1}$ | — | — |
| TP7 | $(1.00E-09)^{-1}$ | $(8.00E-09)^{-1}$ | $(8.00E-09)^{-1}$ |
| TP8 | $(3.00E-09)^{-1}$ | $(3.00E-08)^{-1}$ | — |
| TP9 | $(1.80E-09)^{-1}$ | $(1.00E-08)^{-1}$ | $(6.00E-09)^{-1}$ |

*Estimated

It can be seen that TP1 and TP6 have high affinity for *Thermus aquaticus* DNA polymerase, but little affinity for the other two DNA polymerases. TP2, TP4, TP5 and TP8 have high affinity for the *Thermus aquaticus* and *Thermus thermophilus* DNA polymerases. TP3 has high affinity for the *Thermus aquaticus* and *Thermus filiformis* DNA polymerases. TP7 and TP9 have high affinity for all three DNA polymerases.

Two preferred monoclonal antibodies which are specific for DNA polymerase obtained from *Thermus aquaticus* are identified above as TP4 and TP9 which were prepared using the novel hybridoma cell lines which are identified herein as HB 11126 and HB 11127, respectively, which are available from the American Type Culture Collection (Rockville, Md.). The antibody identified as TP4, and hybridoma HB 11126, are most preferred in the practice of this invention.

It is to be understood that the antibodies described herein as useful temperature sensitive inhibitors for DNA polymerases can also be conjugated with various detection labels, such as avidin, biotin, enzymes, radioisotopes, luminol and other moieties known to one skilled in the art, using conventional procedures. The resulting labeled antibodies can be used in a variety of immunological diagnostic and purification methods. The antibodies can also be attached to various water-insoluble or water-suspendible substrates, including but not limited to, microtiter plates, polymeric and glass particles, synthetic and natural fibers, magnetic particles, test tubes, affinity chromatography matrices, and polymeric and cellulosic films and papers. Attachment can be achieved using adsorption or various covalent attachment techniques.

The composition of the thermostable DNA polymerase and temperature sensitive inhibitor can be supplied and used in a mixture with one or more other PCR reagents, including primers, DNA polymerase cofactors and deoxyribonucleotide-5'-triphosphates, all in a suitable buffer. Representative buffers include, but are not limited to, tris(hydroxymethyl)aminomethane (which is preferred), N,N-bis(2-hydroxyethyl)-2-aminoethanesulfonic acid, 4-(2-hydroxyethyl)-1-piperazinethanesulfonic acid, N-(2-hydroxyethyl)piperazine-N'-(2hydroxypropanesulfonic acid), 3-(N-morpholino)propanesulfonic acid and N[tris(hydroxymethyl)methyl]-2-aminoethanesulfonic acid. Thus, the composition is generally kept at a pH in the range of from about 7.5 to about 9.5, with a pH of from about 8 to about 9 being preferred.

Alternatively, the thermostable DNA polymerase and temperature sensitive inhibitor can be supplied separately from the other reagents needed for PCR. They can be added separately or mixed just prior to use.

The PCR reagents described herein are provided and used in PCR in any concentration suitable for a given process. The minimal amounts of primers, cofactors and deoxyribonucleotide-5'-triphosphates needed for amplification and suitable ranges of each are well known in the art. The amount of complex of DNA polymerase and the inhibitor is generally enough to supply at least about 1 unit of enzyme per 100 μl of reaction mixture once the inhibitor becomes ineffective. Preferably, from about 1 to about 16 units of polymerase per 100 μl of reaction mixture are needed for PCR, and depending upon the particular activity of a given enzyme, the amount of complex is readily determined by one skilled in the art. A "unit" is defined herein as the amount of enzyme activity required to incorporate 10 nmoles of total nucleotides (dNTP's) into an extending nucleic acid chain in 30 minutes at 74° C. The amount of inhibitor present in the composition is generally from about 25 to about 500 moles of inhibitor per mole of DNA polymerase, with from about 50 to about 200 moles of inhibitor per mole of DNA polymerase being preferred.

A target nucleic acid (that is, one to be amplified or detected) can be obtained from any of a variety of sources as noted above. Generally, it is extracted in some manner to make it available for contact with the primers and other PCR reagents. This usually means removing unwanted proteins and cellular matter from the specimen in a suitable manner. Various procedures are known in the art, including those described by Laure et al in *The Lancet*, pp. 538–540 (Sept. 3, 1988), Maniatis et al, *Molecular Cloning: A Laboratory Manual*, pp. 280–281 (1982), Gross-Belland et al in *Eur. J. Biochem.*, 36, 32 (1973) and U.S. Pat. No. 4,965,188. Extraction of DNA from whole blood or components thereof are described, for example, in EP-A-0 393 744 (published Oct. 24, 1990), Bell et al, *Proc. Natl. Acad. Sci. USA*, 78(9), pp. 5759–5763 (1981) and Saiki et al, *Bio/Technology*, pp. 1008–1012 (1985).

Since the nucleic acid to be amplified or detected is usually in double stranded form, the two strands must be separated (that is, denatured) before priming can take place. This can occur during the extraction process, or be a separate step afterwards. Denaturation is accomplished using a heat treatment alone or in combination with any suitable other physical, chemical or enzymatic means as described in the art. Initial denaturation is generally carried out by heating the specimen suspected of containing the targeted nucleic acid at a first temperature of from about 85° to about 100° C. for a suitable time, for example from about 1 second to 3 minutes. This heating will also deactivate the DNA polymerase inhibitor.

The denatured strands are then cooled to a temperature which is generally in the range of from about 55° to about 70° C. The time needed for cooling the denatured strands will vary depending upon the type of apparatus used for the PCR process.

Once the denatured strands are cooled to the second temperature, the reaction mixture containing PCR reagents is incubated at a suitable temperature to effect formation of primer extension products. Generally, this temperature is at least about 50° C., and preferably in the range of from about 65° to about 75° C. The time for incubation can vary widely depending upon the incubation temperature and the length of extension products desired, but in preferred embodiments, it is from about 1 to about 120 seconds.

The primer extension products thus formed can be detected in a suitable manner while as hybridized products, or denatured either for detection of a single strand or further cycling in PCR.

If the hybridized primer extension products are denatured, PCR can be carried out further in as many cycles of priming, extension and denaturation as desired. Generally, at least 20 cycles will be carried out, with from 20 to 50 cycles being preferred.

After denaturation the last time in the assay, the final primer extension products can be detected using known procedures, as described below. Alternatively, the primer extension products can be detected in undenatured form using known procedures such as agarose gel electrophoresis with ethidium bromide staining.

The amplification method of this invention is preferably conducted in a continuous, automated manner so that the reaction mixture is temperature cycled in a controlled manner for desired preset times. A number of instruments have been developed for this purpose, as one of ordinary skill in the art would know.

One such instrument for this purpose is described in some detail in U.S. Pat. No. 4,965,188 and EP-A-0 236 069, and involves moving liquids from one temperature environment to another under controlled conditions.

Another instrument utilizes temperature cycling without a liquid handling system, and is described in some detail in U.S. Pat. No. 4,965,188 and EP-A-0 236 069. Generally, this instrument includes a heat conducting container for holding a number of reaction tubes containing reaction mixture, a means for heating, cooling and temperature maintenance, and a computing means to generate signals to control the amplification sequence, changes in temperature and timing.

A gas chromatograph has also been used for amplification, as described for example by Hoffman et al, *Biotechniques,* 6(10), pp. 932–936 (1988), and amplification in a "teacup" has been described as a simple and inexpensive technique [Innis et al (Eds.), *PCR Protocols: A Guide to Methods and Applications,* Chapter 51, pp. 429–434 by Robert Watson, Academic Press, Inc., 1990].

A preferred instrument for processing amplification reactions in a disposable chemical test pack is described in some detail in EP-A-0 402,994 (published Dec. 19, 1990). In general, this instrument comprises a surface for supporting a chemical test pack, pressure applicators supported above the surface for acting on the reaction pack transfer fluids between adjacent chambers in the test pack, and means for operating the pressure applicators through a range of movement extending across the test pack.

EP-A-0 402 994 provides details of useful chemical test packs which can be processed using the instrument described in that same publication. Also described therein are means for heating and cooling the test pack at repeated intervals (that is, through cycles) appropriate for the method of the present invention. As noted above, while these instruments and test packs are preferred in practicing the present invention, they are not considered essential to obtaining the beneficial results noted herein.

The method of this invention can be used to advantage to rapidly detect or characterize a target nucleic acid which is present in an infectious agent. Detection can be accomplished in a number of known ways, such as those described in U.S. Pat. No. 4,965,188. For example, the amplified nucleic acid can be analyzed using Southern blotting techniques. Alternatively, amplification can be carried out using radioisotopic or biotinylated primers which can then be detected using appropriate techniques. Sequence specific oligonucleotides can be used with dot blot techniques to detect single-base pair variations in nucleic acids.

In one preferred embodiment, once a desired amount of the target nucleic acid of interest has been generated and the primer extension products are denatured for a last time, the amplified target nucleic acid is detected using an oligonucleotide probe which is labeled for detection and can be directly or indirectly hybridized with one of the primer extension products. Procedures for attaching labels and preparing probes are well known in the art, for example, as described by Agrawal et al, *Nucleic Acid Res.,* 14, pp. 6227–45 (1986), U.S. Pat. No. 4,914,210 (Levenson et al) relating to biotin labels, U.S. Pat. No. 4,962,029 (Levenson et al) relating to enzyme labels, and the references noted therein. Useful labels include radioisotopes, electron-dense reagents, chromogens, fluorogens, phosphorescent moieties, ferritin and other magnetic particles (see U.S. Pat. No. 4,795,698 of Owen et al and U.S. Pat. No. 4,920,061 of Poynton et al), chemiluminescent moieties and enzymes (which are preferred). Useful enzymes include, glucose oxidase, peroxidases, uricase, alkaline phosphatase and others known in the art and can be attached to oligonucleotides using known procedures. Substrates and dye forming compositions for such enzymes are well known.

Where the label is a preferred enzyme such as a peroxidase, at some point in the assay, hydrogen peroxide and suitable dye-forming compositions are added to provide a detectable dye. For example, useful dye-providing reagents include tetramethylbenzidine and derivatives thereof, and leuco dyes, such as triarylimidazole leuco dyes (as described in U.S. Pat. No. 4,089,747 of Bruschi), or other compounds which react to provide a dye in the presence of peroxidase and hydrogen peroxide. Particularly useful dye-providing compositions are described in EP-A-0 308 236 (published Mar. 22, 1989).

Detection of the presence of the probe with the complementary product can be achieved using suitable detection equipment and procedures which are well known. Certain probes may be visible to the eye without the use of detection equipment.

In a preferred embodiment, one or both of the primers are biotinylated and the amplified nucleic acid is detected using detectably labeled avidin or a derivative. For example, avidin can be conjugated with an enzyme, or have a radioactive moiety. Biotin on the amplified product complexes with the avidin, and appropriate detection techniques are used.

Other formats for detection are well known in the art which includes standard hybridization procedures (such as "sandwich assays), and other procedures described in the amplification art such as U.S. Pat. No. 4,965,188.

It is also useful for the method of this invention to be carried out in a suitable container. The most crude container would be a test tube, cuvette, flask or beaker, but more sophisticated containers have been fashioned in order to facilitate automated procedures for performing the method (see for example, WO-A-91/12342). For example, cuvette and chemical test packs (also known as pouches), constructed to provide certain temperature characteristics during the practice of the method, are described in U.S. Pat. No. 4,902,624 (Columbus et al) and EP-A-0 381 501 (published Aug. 8, 1990). Such test packs have a multiplicity of reaction chambers having various reagents, buffers and other materials which are useful at various stages in the amplification or detection method. The packs can be appropriately and rapidly heated and cooled in cycles to promote the various steps of the amplification method of this invention. Other useful containers could be suitably fashioned for automated or single use of the method of this invention.

In order for the amplified product to be detected, it is often useful (but not necessary) for it to be separated from the other materials in the reaction medium. This is done by any of a number of ways, including using a water-insoluble capture means on a primer or probe so that the primer extension products which are replicated in the method are water-insolubilized and removed from the reagent mixture. Primers or probes can be attached to insoluble materials in a suitable manner, or they can be designed to be capturable, that is, reactive with a capture means at some point in the method.

One useful capture means is described in EP-A-0 370 694 (published May 30, 1990). A primer has a specific binding ligand attached thereto (such as biotin, an antibody or a lectin) which is capable of specifically binding to a receptor molecule (such as avidin, an antigenic material or a sugar) which is bound in a suitable manner to an insoluble material such as polymeric particles. The resulting insolubilized specifically bound product can be separated from water-soluble materials by filtration, centrifugation or other suitable separation techniques. Detection of the captured nucleic acid strand can be accomplished directly using a probe complementary thereto, or indirectly using one or more intermediate oligonucleotides to which a labeled probe can be hybridized.

Alternatively, the amplified product can be separated from undesired materials by using an oligonucleotide complementary thereto, which oligonucleotide is attached to an insoluble substrate (such as polymeric particles) using known attachment techniques. One such technique is described in EP-A-0 439,222 (published Sept. 18, 1991). Other techniques are described for example in U.S. Pat. No. 4,713,326 (Dattagupta et al), WO-A-88/01302 (published Feb. 25, 1988) and EP-B-0 070 687 (published Jan. 26, 1983) whereby intermediate oligonucleotides are used in a hybridized product of multiple components to which the capture oligonucleotide and amplified nucleic acid are joined.

Useful separation means are microporous filtration membranes such as the polyamide membranes marketed by Pall Corp. (for example as LOPRODYNE™ or BIODYNE™ membranes). They can be used uncoated or precoated with surfactants or other materials which facilitate the analytical procedures.

The membranes can be used as a separate substrate with suitable containers for carrying out other steps of the assay. Preferably, however, they are mounted as part of a disposable test device. Various disposable test devices are known in the art including those described in U.S. Pat. No. 3,825,410 (Bagshawe), U.S. Pat. No. 3,888,629 (Bagshawe), U.S. Pat. No. 3,970,429 (Updike) and U.S. Pat. No. 4,446,232 (Liotta). Particularly useful devices are described in U.S. Pat. No. 4,921,677 (Hinckley et al) and are commercially available as SURECELL™ test devices and assay kits from Eastman Kodak Company.

Any useful solid support can be used for separation of water-insoluble product for detection, including a microtiter plate, test tube, beaker, beads, film, membrane filters, filter papers, gels, magnetic particles or glass wool. It can be made of a number of materials including glass, ceramics, metals, naturally occurring or synthetic polymers, cellulosic materials, filter materials and others readily apparent to one of ordinary skill in the art. Particularly useful solid support materials are polymeric beads generally having an average particle size of from about 0.1 to about 10 μmeters.

The detection can also be carried out by immobilizing a capture probe on a flat substrate, such as the microporous filtration membranes described above, or on thin polymeric films, film laminates, uncoated papers or polymer coated papers, a number of which are known in the art. Other details about such materials are provided in EP-A-0 408 738 (published Jan. 23, 1991).

Although this disclosure has focused on the use of the claimed composition and test kit in PCR, the invention is also useful in other procedures for enzymatic replication of nucleic acids, such as the transcription based amplification technique described by Kwoh et al, *Proc. Natl. Acad. Sci. USA* 87:1974, 1989, nucleic acid ligase techniques described by Wu et al, *Genomics* 4:560, 1989 and Barringer et al, *Gene* 89:117, 1990, and ribonuclease H cleavage of DNA-RNA-DNA probes annealed to nucleic acid targets.

The following examples are included to illustrate the practice of this invention, and are not meant to be limiting in any way. All percentages are by weight unless otherwise noted.

Materials and Methods for Examples:

Recombinant DNA polymerase from *Thermus aquaticus* was prepared as described in U.S. Ser. No. 602,848 (filed Oct. 26, 1990 by Sullivan), which corresponds to EP-A-0 482 714 (published Apr. 29, 1992), and had an activity of about 250,000 units/mg of protein. The activity can vary depending upon the source and procedure for obtaining the enzyme.

The antibodies specific for the noted DNA polymerase were obtained by using the conventional procedures described above for the preparation of monoclonal antibodies.

The primers used in Example 3 were prepared using known starting materials and procedures using an Applied Biosystems Model 380B DNA synthesizer and had the following sequences:

---

SEQ ID NO: 1:
5'-ATAATCCACC TATCCCAGTA GGAGAAAT-3'
SEQ ID NO: 2:
5'-X-TTTGGTCCTT GTCTTATGTC CAGAATGC-3'

--- wherein X represents a biotin moiety attached to the sequence through two tetraethylene glycol spacer units using the teaching of U.S. Pat. No. 4,914,210 (Levenson et al).

A target nucleic acid from HIV-I DNA isolated from HUT/HIV AAV 78 was obtained from Dr. Bernard Poiesz at SUNY Health Science Center at Syracuse, N.Y. The primers were complementary to double strands of the target along a nucleic acid sequence in the gag region (nucleotides 1541–1655).

Deoxyribonucleotides (dNTP's) were obtained from Sigma Chemical Co.

Other reagents and materials were obtained either from commercial sources or prepared using readily available starting materials and conventional procedures.

EXAMPLE 1

Determination of Inhibitory Effect of Various Antibodies Specific to Thermostable DNA Polymerase Several antibodies specific to DNA polymerase from *Thermus aquaticus* were evaluated for their ability to inhibit the activity of the enzyme. The antibodies so tested and the results of the tests are listed in Tables II and III below.

The DNA polymerase (50 units/ml, 2.22 nmolar) was assayed by incubating it with antibody (37.5 µg/ml, 250 nmolar) in tris(hydroxymethyl)aminomethane buffer (17.5 mmolar, pH 8.0) containing magnesium chloride (5 mmolar), potassium chloride (25 mmolar), sodium chloride (75 mmolar), 2-mercaptoethanol (0.5 mmolar), gelatin (0.5 mg/ml), NONIDET™ P-40 nonionic surfactant (0.25%, Shell Chemicals) and TWEEN™ 20 nonionic surfactant (0.25%, ICI Americas) for 10 minutes at room temperature. The following materials were then added to a final volume of 50 µl in order to initiate polymerization: N-tris(hydroxymethyl)methyl-3-aminopropanesulfonic acid buffer (25 mmolar, pH 9.8), magnesium chloride (10 mmolar), potassium chloride (50 mmolar), 2-mercaptoethanol (1 mmolar), activated salmon testes DNA template (0.29 µg/µl), dCTP, dGTP and dTTP (200 µmolar of each), and $^3$H-dATP (100 µmolar, 0.02 µCi/µl). Activated salmon testes DNA template is a double-stranded molecule which has gaps in portions of either strand, which gaps are filled by the appropriate dNTP's using the DNA polymerase. The resulting mixture (containing 0.89 nmolar of DNA polymerase and 100 nmolar of antibody) was incubated at 37° C. ($T_1$) for 240 minutes.

The activity of the DNA polymerase was then measured as units/ml by determining the amount of radioactivity that was incorporated into acid precipitable material and converting this to tens of nucleotides incorporated in this mixture under these conditions in 30 minutes by one ml of undiluted enzyme. The inhibition effect of the antibody (or mixture) was measured as "% of Control" in reference to the test where no antibody was present and the DNA polymerase had 100% of its theoretical activity.

The results of the tests are presented below in Table II.

TABLE II

| Antibody | Units/ml | % of Control A |
|---|---|---|
| None (Control A) | 3083 | 100.0 |
| None (Control B - no enzyme) | −9 | −0.3*** |
| TP1 | 888 | 28.8 |
| TP2 | 2687 | 87.2 |
| TP3 | 1983 | 64.3 |
| TP4 | 43 | 1.4 |
| TP5 | 214 | 7.0 |

TABLE II-continued

| Antibody | Units/ml | % of Control A |
|---|---|---|
| TP6 | 2313 | 75.0 |
| TP7 | 628 | 20.4 |
| TP8 | 460 | 14.9 |
| TP9 | 271 | 8.8 |
| TP10 | 2740 | 88.9 |
| TP11 | 2830 | 91.8 |
| HB9421* | 2859 | 92.7 |
| TIB169** | 3152 | 102.2 |
| TP14 | 11 | 0.3 |

*Rat monoclonal antibody specific to creatine kinase, prepared from hybridoma deposited with the ATCC as HB9421 which is readily available to the public.
**Mouse monoclonal antibody specific to rat kappa chain, prepared from the hybridoma deposited with the ATCC as TIB169 which is readily available to the public.
***Negative values are within experimental error.

These data indicate that the monoclonal antibodies (type IgG) identified as TP1, TP4, TP5 and TP7 through TP9 exhibited very useful inhibition of the DNA polymerase. The IgG monoclonal antibodies labeled as TP2, TP3 and TP6 and the IgM monoclonal antibodies labeled as TP10 and TP11 were not as effective in this particular experiment, but other conditions may be found to render them more effective according to the present invention. HB9421 and TIB169 were monoclonal antibodies of the IgG class which were not specific to DNA polymerase and served as "negative controls" in the experiment. TP14 was a mixture including TP1 through TP11, and showed effective inhibition of DNA polymerase activity.

A number of the antibodies listed in Table II above were tested to see if they were inactivated at 74° C. (T2). The DNA polymerase (2 units/ml, 0.089 nmolar) was assayed by mixing it with N-tris(hydroxymethyl)methyl-1,3-aminopropanesulfonic acid buffer (25 mmolar, pH 8.9), magnesium chloride (10 mmolar), potassium chloride (50 mmolar), 2-mercaptoethanol (1 mmolar), activated salmon testes DNA template (0.29 µg/µl), and antibody (1.5 µg/ml, 10 nmolar) in a total volume of 50 µl. Reaction was initiated by adding a mixture of each of dCTP, dGTP and dTTP (200 µmolar of each) along with 3H-dATP (100 µmolar, 0.02 µCi/µl) to complete the 50 µl final volume. The resulting mixture was incubated at 74° C. for 10 minutes. The amount of activity was determined and is shown in Table III below.

TABLE III

| Antibody | Units/ml | % of Control A |
|---|---|---|
| None (Control A) | 317,000 | 100.0 |
| None (Control B - no enzyme) | 650 | 0.2 |
| TP1 | 142,000 | 44.9 |
| TP4 | 119,000 | 37.7 |
| TP5 | 202,000 | 63.7 |
| TP7 | 223,000 | 70.5 |
| TP8 | 103,000 | 32.5 |
| TP9 | 134,000 | 42.2 |
| TP14 | 14,000 | 4.5 |

These data show that the monoclonal antibodies identified as TP1, TP4, TP5 and TP7–TP9 were at least partially inactivated after 10 minutes incubation at 74° C. At higher $T_2$ temperatures, for example 90°–95° C., the inactivation of the antibodies is even greater. Other conditions may be readily found to completely inactivate the antibodies. The mixture identified as TP14 and the polyclonal antibodies (TP15 and TP16) were not significantly inactivated at 74° C., but other conditions may be readily found to inactivate the antibodies present to an acceptable degree.

The antibodies identified as TP1 through TP9 and the mixture identified as TP14 thus were found to complex with the DNA polymerase to at least some extent, inactivating that enzyme at low temperatures ($T_1$), and to some extent being inactivated themselves at the higher temperature ($T_2$).

EXAMPLE 2

PCR Protocol Using Inactivating Antibodies

This example demonstrates the use of some of the antibodies described in Example 1 in a PCR method for the detection of a target nucleic acid, namely HIV-I DNA.

The resulting PCR reaction mixture contained tris(hydroxymethyl)aminomethane buffer (10 mmolar, pH 8), potassium chloride (50 mmolar), magnesium chloride (10 mmolar), gelatin (0.1 mg/ml), each of the primers identified above as SEQ ID NO:1 and SEQ ID NO:2 (1 μmolar of each), dATP, dCTP, dGTP and dTTP (1.5 mmolar of each), human placental DNA (2 μg), DNA polymerase obtained from *Thermus aquaticus* (32 units/200 μl, 7.1 nmolar), and antibody (24 μg/200 μl, 800 nmolar). The target nucleic acid was present at 2,000 copies/200 μl.

The DNA polymerase and antibody were mixed prior to addition of the remaining reagents and allowed to incubate at 22° C. ($T_1$) for ten minutes to form a complex of enzyme and antibody. One sample (identified as "i") of each PCR mixture was used immediately, while another sample (identified as "l") was incubated for an additional five hours at room temperature prior to use. The antibodies specific to the DNA polymerase are identified in Table I above.

The PCR protocol was as follows and was carried out in a 0.5 ml microcentrifuge tube using a commercially available Perkin Elmer Thermal Cycler:

The target DNA was denatured by heating it to 95° C. ($T_2$) for about 15 seconds. After cooling to 65° C., primer extension products were formed for about 40 seconds, followed by denaturation again at 95° C. The cycle of primer extension and denaturation was carried out 35 times.

The results of PCR were detected by conventional gel electrophoresis using a 4% agarose gel and ethidium bromide staining using conventional procedures. These results are shown in the FIGURE and in Table IV below. The antibodies are identified as those described in Table II above. Table IV also shows the results of PCR as determined using a capture probe comprised of an oligonucleotide complementary to the target nucleic acid, which oligonucleotide is attached to a polymeric particle.

Detection using the capture probe was carried out using a test device similar to that described in U.S. Pat. No. 4,921,677 which has uncoated nylon microporous membranes (LOPRODYNE™ from Pall Corp.) in each of three test wells. Dried on each membrane was a deposit (1 μl, 0.5% solids) of poly[styrene-co-3-(p-vinylbenzylthio)propionic acid] (97.6:2.4 monomer molar ratio) beads (1 μm average diameter) to which an oligonucleotide complementary to a sequence of the gag region of HIV-I DNA had been covalently attached using known technology to form a capture probe for HIV-I DNA.

The capture probe oligonucleotide had the following sequence:

SEQ ID NO: 3:
5'- ATCCTGGGAT TAAATAAAAT AGTAAGAATG TATAGCCCTA C-3'

Also deposited on each membrane in a similar fashion in a separate location was a capture probe for a nucleic acid sequence of β-globin DNA to detect nonspecific background. The probe was prepared from the same polymeric particles and comprised an oligonucleotide having the sequence:

SEQ ID NO: 4:
5'-CCTCAAACAG ACACCATGGT GCACCTGACT C-3'

The deposited probes were allowed to dry for 15–30 minutes. The amplified nucleic acid products from PCR were diluted 1:20 in a solution of tris(hydroxymethyl)aminomethane buffer (10 mmolar, pH 8), potassium chloride (50 mmolar), gelatin (0.1 mg/ml) and magnesium chloride (10 mmolar), heated to 95° C. for five minutes to denature nucleic acid strands, and pipetted (100μl) into each test well of the test device. The test devices were then incubated at 42° C. for five minutes to allow hybridization of the amplified PCR products with the capture probes. The test wells were washed with a solution (250μl) of sodium phosphate (0.025 molar, pH 7.4), sodium chloride (0.37 molar), ethylenediaminetetraacetic acid (2.5 mmolar), ethylmercurithiosalicyclic acid, sodium salt (0.25 mmolar) and sodium decyl sulfate (1%) which had been heated to 55° C. To the test wells was then added a solution (50μl) of a conjugate of streptavidin-horseradish peroxidase (312 ng/l) in 3-morpholinopropanesulfonic acid buffer (100 mmolar, pH 7.5) and sodium phosphate (0.25 molar) containing sodium chloride (0.075 molar), ethylmercurithiosalicyclic acid, sodium salt (0.25 mmolar), 4'-hydroxyacetanilide (0.01 molar) and casein (0.5%), followed by incubation at room temperature for two minutes.

Following a second wash (250 μl heated to 55° C.), a solution (100 μl) of the triarylimidazole leuco dye 4,5-bis(4-dimethylaminophenyl)-2-(4-hydroxy-3,5-dimethoxyphenyl)imidazole (0.1 g/l), polyvinylpyrrolidone (12.5 g/l), diethylenetriamine-pentaacetic acid (0.01 mmolar), 4-hydroxyacetanilide (5 mmolar), hydrogen peroxide (0.1%) and sodium phosphate (0.01 molar, pH 6.8) was added to each test well, followed by incubation at room temperature for two minutes. A solution of sodium azide (0.1%) was added to stop the formation of dye, and the resulting dye signal was compared to a color chart (values 0 to 10 in density).

TABLE IV

| PCR Experiment (two runs of each) | Gel Results | | Capture Probe Results** | |
|---|---|---|---|---|
| | Product* | Primer/ Dimer? | Signal | Background |
| −T, −Ab i | 0 | yes | 0 | 0 |
| −T, −Ab i | 0 | yes | 0 | 0 |
| −T, −Ab l | 0 | yes (smear) | 0 | 0 |
| −T, −Ab l | 0 | yes (smear) | 0 | 0 |
| +T, −Ab i | 3 | yes (faint) | 7 | 0 |
| +T, −Ab i | 3 | yes (faint) | 6.5 | 0 |
| +T, −Ab l | 1 | yes | 5 | 0 |
| +T, −Ab l | 1 | yes | 3 | 0 |
| +T, +TP3, i | 2.5 | no | 7 | 0 |
| +T, +TP3, i | 2.5 | no | 7 | 0 |
| +T, +TP3, l | 2 | yes (smear) | 7 | 0 |
| +T, +TP3, l | 2 | yes (smear) | 7 | 0 |
| +T, +TP5, i | 0.5 | no | 3 | 0 |
| +T, +TP5, i | 2 | no | 4 | 0 |
| +T, +TP5, l | 1.5 | no | 7 | 0 |
| +T, +TP5, l | 1 | no | 5 | 0 |
| +T, +TP7, i | 3 | no | 7 | 0 |

TABLE IV-continued

| PCR Experiment (two runs of each) | Gel Results | | Capture Probe Results** | |
|---|---|---|---|---|
| | Primer/ | | | |
| | Product* | Dimer? | Signal | Background |
| +T, +TP7, i | 3 | no | 7 | 0 |
| +T, +TP7, l | 2.5 | no | 6 | 0 |
| +T, +TP7, l | 3 | no | 7 | 0 |
| +T, +TP8, i | 3 | no | 6 | 0 |
| +T, +TP8, i | 3 | no | 7 | 0 |
| +T, +TP8, i | 3 | no | 7 | 0 |
| +T, +TP8, i | 2.5 | no | 7 | 0 |
| +T, +TP9, i | 2.5 | no | 5 | 0 |
| +T, +TP9, i | 3 | no | 6 | 0 |
| +T, +TP9, l | 3 | no | 6 | 0 |
| +T, +TP9, l | 3 | no | 7 | 0 |
| +T, +TP10, i | 3 | no | 7 | 0 |
| +T, +TP10, i | 3 | no | 7 | 0 |
| +T, +TP10, l | 0.5 | yes (much) | 4 | 0 |
| +T, +TP10, l | 1 | yes (smear) | 6 | 0 |
| +T, +TP12, i | 1 | yes (faint) | 5 | 0 |
| +T, +TP12, i | 3 | yes (faint) | 7 | 0 |
| +T, +TP12, l | 0.5 | yes (much) | 2 | 0 |
| +T, +TP12, l | 0.5 | yes (much) | 3 | 0 |
| +T, +TP14, i | 3 | no | 6 | 0 |
| +T, +TP14, i | 3 | no | 6 | 0 |
| +T, +TP14, l | 0.5 | no | 1 | 0 |
| +T, +TP14, l | 2.5 | no | 4 | 0 |
| +T, +TP15, i | 0 | no | 0 | 0 |
| +T, +TP15, i | 0 | no | 0 | 0 |
| +T, +TP15, l | 0 | no | 0 | 0 |
| +T, +TP15, l | 0 | no | 0 | 0 |

+T refers to target HIV-I DNA being present
−T refers to target HIV-I DNA being absent
+Ab refers to antibody being present
−Ab refers to antibody being absent
*Gel results were quantified as from 0 (no band) to 5 (highest density) band
**Capture probe results were quantified as visible dye signal from 0 (no density) to 10 (highest density)

The results shown in Table IV and in the FIGURE indicate that without the presence of antibody specific to the DNA polymerase, only primer dimer and non-specific products are produced in the absence of target DNA (see first two gel strips labeled "-T, -Ab", both "i" and "l"). In the next two gel strips which represent a negative control (no target nucleic acid) in the presence of inhibiting antibody, the only visible bands are unused primers. These tests alone demonstrate that the antibody effectively inhibits the activity of the DNA polymerase and prevents the formation of non-specific products.

Antibodies TP5, TP7, TP8, TP9 and TP14 (mixture) are within the scope of this invention, and allowed the production of target nucleic acid only, both when the PCR mixture was used immediately (i) and after five hours incubation (l). The yields of specific product varied with different antibodies, and some of them allowed the formation of some non-specific products. However, one skilled in the art would be able to readily adapt a given antibody to a given target nucleic acid and PCR conditions to optimize the reduction in formation of such products. Some antibodies were best used immediately upon mixing with PCR reagents while others were also useful after the five hour incubation period. The better antibodies under the conditions used in this example appeared to be the monoclonal antibodies of the IgG class.

Antibodies labeled as TP14 and TP15 were polyclonal antibodies specific to the DNA polymerase which did not work well under the conditions of this example, but which may be useful in the practice of the invention under other conditions.

EXAMPLE 3

Evaluation of Antibodies For Inactivation

The conditions necessary to inactivate the antibodies useful in the practice of this invention were determined in the following manner.

DNA polymerase from *Thermus aquaticus* was incubated with each antibody at room temperature ($T_1$) as described above in Example 1 except that the DNA polymerase was at 5 units/ml (0.222 nmolar), and the antibody was present at 3.75 μg/ml (25 nmolar). After this incubation, a solution of N-tris(hydroxymethyl)methyl-3-aminopropanesulfonic acid buffer (27.78 mmolar, pH 9.8), magnesium chloride (11.11 mmolar), potassium chloride (55.56 mmolar), 2-mercaptoethanol (1.11 mmolar) and activated salmon testes DNA template (0.32 μg/μl) was added to make a final volume of 45μl of solution (containing 0.099 nmolar DNA polymerase and 11.11 nmolar antibody). This solution was heated in an Ericomp™ thermocycler (commercially available from Ericomp, Inc.) for 1 minute at 85° C. ($T_2$), cooled to room temperature and then kept on ice for at least 5 minutes. The reaction was then begun by the addition of a solution (5μl) of dCTP, dGTP and dTTP (2 mmolar of each) and $^3$H-dATP (1 mmolar, 0.2 μCi/μl). The resulting mixture, now having 0.089 nmolar DNA polymerase and 10 nmolar antibody was incubated for 10 minutes at 74° C.

The activity of the DNA polymerase after this incubation was measured as described above in Example 1. The inhibition effect of the residual antibody activity was measured as a "% of Control" in reference to the test where no antibody was present and the DNA polymerase had 100% of its theoretical activity. The results of the tests are provided in Table V below.

TABLE V

| Antibody | Enzyme Activity (Units/ml) | % of Control A |
|---|---|---|
| Experiment A: | | |
| Control A (none, no preheating) | 336,000 | 100 |
| Control B (none, no enzyme) | 0 | 0 |
| Control C (none, preheated) | 341,000 | 101* |
| TP4 | 331,000 | 98.5* |
| TP5 | 349,000 | 104 |
| TP9 | 340,000 | 101* |
| TP14 | 296,000 | 88.1 |
| Experiment B: | | |
| Control A (none, no preheating) | 368,000 | 100 |
| Control B (none, no enzyme) | 0 | 0 |
| Control C (none, preheated) | 354,000 | 96.2 |
| TP1 | 359,000 | 97.5* |
| TP7 | 362,000 | 98.3* |
| TP8 | 350,000 | 94.9 |

*Within experimental error of 100%

These data indicate that the DNA polymerase is completely stable at 85° C. for 1 minute (Control C vs. Control A). Further, the data demonstrate that each of the antibodies, already shown to be significant inhibitors of DNA polymerase activity (Table II above), are completely or nearly completely inactivated by the heat treatment noted above, thereby allowing full activity by the DNA polymerase. These data support our conclusion that these antibodies are useful DNA polymerase inhibitors for amplification methods, such as PCR.

EXAMPLE 4

Use of Antibodies to DNA Polymerase in PCR to Provide Improved Sensitivity

This example demonstrates the use of the antibodies described herein to improve the sensitivity of PCR methods as compared to a PCR method where the antibodies were not used.

The antibody identified herein as TP9 was used in the tests described below. Human patient samples obtained from Dr. Bernard Poiesz were evaluated, the HIV-I DNA content having been determined by standard procedures and reported as the total number of copies in the sample before amplification. The patient samples were divided into four categories for two separate test groups as specified on the electrophoresis gel matrices, the four categories being "high positive", "medium positive", "low positive" and "negative".

The assays were carried out in self-contained test devices like those described in EP-A-0 402 994, and after amplification, the reaction mixture was transferred to microfuge tubes for detection using either gel electrophoresis or a capture probe in a disposable test device as described in Example 2 above using procedures described in EP-A-0 408 738.

In the amplification procedure, two sets of primers were used to detect nucleic acid sequences in both the gag and env regions of HIV-I DNA, and thus two separate products were observed on the electrophoresis gel. The primers for the region are identified below as SEQ ID NO:5 and SEQ ID NO:6, whereas the primers for the env region are identified below as SEQ ID NO:7 and SEQ ID NO:8. These primers had the following sequences:

---
SEQ ID NO: 5:
5'-X-AGTGGGGGGA CATCAAGCAG CCATGCAA-3'
SEQ ID NO: 6:
5'-X-TTCCTGCTAT GTCACTTCCC CTTGGTTC-3'
SEQ ID NO: 7:
5'-X-TAGCACCCAC CAGGGCAAAG AGAAGAGT-3'
SEQ ID NO: 8:
5'-X-AGATGCTGTT GCGCCTCAAT AGCCCTCA-3'
--- wherein "X" represents a biotin moiety connected to the sequence through two tetraethylene glycol spacer units using the procedure described in U.S. Pat. No. 4,914,210. The primers were synthesized using standard starting materials and procedures on a commercially available ABI 380B DNA synthesizer and Applied Biosystems 1 μmolar CPG columns.

The PCR reaction mixture contained potassium chloride (50 molar), magnesium chloride (10 molar), tris(hydroxymethyl)aminomethane buffer (10 molar), gelatin (0.1 mg/ml), ethylenediaminetetraacetic acid (1 mmolar), glycerol (9.5% v/v), dNTP's (1.5 mmolar of each of dATP, dCTP, dGTP and dTTP), four oligonucleotide primers (1 μmolar of each) as described above, a patient sample containing target DNA (16.3 μg/ml), TP9 antibody (0.107 mg/ml) and DNA polymerase (from *Thermus aquaticus*, 160 units/ml).

The patient samples were obtained from patients either known to be infected with HIV-I or believed to be free of that virus. The DNA had been obtained from the patient samples using standard phenol/chloroform extraction of peripheral blood mononuclear cells. The TP9 antibody was mixed with the DNA polymerase and incubated at room temperature for 10 minutes with gentle agitation prior to addition to the other components to form the PCR reaction mixture. In the Control reactions, the TP9 was omitted and replaced with a solution of tris(hydroxymethyl)aminomethane (10 mmolar), ethylenediaminetetraacetic acid (1 mmolar).

Samples (200μl) of the PCR reaction mixtures were placed into the reagent chambers of test packs as described above, and PCR amplification was carried out using a thermocycler which is described in EP-A-0 402 994 (published Dec. 19, 1990), and the protocol:

90° C. preheating for 120 seconds, and
40 cycles of:
  92° C. for 30 seconds, and
  70° C. for 80 seconds.

For half of the samples, amplification was carried out immediately after putting the reagents in the reagent chambers. For the remaining samples, amplification was carried out after the test packs had stayed at room temperature for 2 hours.

After amplification, the fluid in the reagent chambers was placed into microfuge tubes, and the PCR products were analyzed both by size separation on a 4% agarose gel, stained with ethidium bromide, and by a detection system (like that described in Example 2 above) using a capture probe.

The results on the gel indicated that the amount of primer-dimer formed in the presence of TP9 was greatly reduced. The use of the antibody also increased amplification efficiency. In particular, the use of the antibody increased the amplification efficiency when amplification was delayed. Where the antibody was not present, amplification was not possible in the delayed samples.

The results of the capture probe tests are shown in Table VI below:

TABLE VI

| Patient | Immediate PCR | | PCR 2 Hours Later | |
|---|---|---|---|---|
| | +TP9 | −TP9 | +TP9 | −TP9 |
| high positive | + | + | + | − |
| high positive | + | + | I* | − |
| medium positive | + | + | + | − |
| medium positive | + | + | + | I* |
| low positive | − | + | + | − |
| low positive | + | + | + | − |
| negative | I* | − | − | − |
| negative | + | I* | − | − |

*"I" refers to indeterminate result, which means 1 primer set was positive while the other primer set was negative.

The results using a capture probe were consistent with those observed with the gel/ethidium bromide staining experiments.

The invention has been described in detail with particular reference to preferred embodiments thereof, but it will be understood that variations and modifications can be effected within the spirit and scope of the invention.

We claim:

1. A composition comprising a thermostable DNA polymerase, and a temperature sensitive inhibitor for said DNA polymerase, said inhibitor being an antibody which is specific to said thermostable DNA polymerase and which inhibits said thermostable DNA polymerase at a temperature $T_1$ which is less than about 85° C. such that enzymatic activity of said thermostable DNA polymerase is inhibited, and said inhibitor being irreversibly inactivated at a temperature $T_2$ which is greater than $T_1$ and is also greater than about 40° C., so that said thermostable DNA polymerase regains its enzymatic activity, wherein said thermostable DNA polymerase is stable at $T_2$.

2. The composition of claim 1 wherein $T_2$ is at least about 5° C. above $T_1$.

3. The composition of claim 1 wherein said thermostable DNA polymerase is isolated from a species of Thermus, or is a recombinant form thereof.

4. The composition of claim 1 wherein said thermostable DNA polymerase is an enzyme isolated from *Thermus aquaticus, Thermus thermophilus, Thermus filiformis, Thermus flavus, Pyrococcus furiosus, Thermococcus litoralis*, a Thermotoga species or a recombinant form of any of these.

5. The composition of claim 1 comprising two or more of said temperature sensitive inhibitors which or different antibodies specific to said thermostable DNA polymerase.

6. The composition of claim 1 wherein said antibody is a monoclonal antibody of the IgG class which has an association constant of at least about $1 \times 10^7$ molar$^{-1}$ with said DNA polymerase.

7. The composition of claim 1 wherein said monoclonal antibody is produced by the hybridoma cell line ATCC HB 11126.

8. The composition of claim 1 further comprising an additional PCR reagent.

9. A kit for polymerase chain reaction comprising, in separate packaging:

a. a composition comprising a thermostable DNA polymerase, and a temperature sensitive inhibitor for said DNA polymerase, said inhibitor being an antibody which is specific to said thermostable DNA polymerase and which inhibits said thermostable DNA polymerase at a temperature $T_1$ which is less than about 85° C. such that enzymatic activity of said thermostable DNA polymerase is inhibited, and said inhibitor being irreversibly inactivated at a temperature $T_2$ which is greater than $T_1$ and is also greater than about 40° C., so that said thermostable DNA polymerase regains its enzymatic activity, and b. at least one additional PCR reagent,
   wherein said thermostable DNA polymerase is stable at $T_2$.

10. The kit of claim 9 wherein said temperature sensitive inhibitor is a monoclonal antibody of the IgG class which has an association constant of at least about $1\times10^7$ molar$^{-1}$ with said DNA polymerase.

11. A kit for PCR comprising, in separate packaging:

a. a thermostable DNA polymerase, and b. a temperature sensitive inhibitor for said thermostable DNA polymerase,
   said inhibitor being an antibody which is specific to said thermostable DNA polymerase and which inhibits said thermostable DNA polymerase at a temperature $T_1$ which is less than about 85° C. such that enzymatic activity of said thermostable DNA polymerase is inhibited, and
   said inhibitor being irreversibly inactivated at a temperature $T_2$ which is greater than $T_1$ and is also greater than about 40° C., so that said thermostable DNA polymerase regains its enzymatic activity,
   wherein said thermostable DNA polymerase is stable at $T_2$.

12. The kit of claim 11 wherein said temperature sensitive inhibitor is a monoclonal antibody of the IgG class which has an association constant of at least about $1\times10^7$ molar$^{-1}$ with said DNA polymerase.

13. The kit of claim 11 further comprising at least one additional PCR reagent.

14. A monoclonal antibody which is specific to a thermostable DNA polymerase, said antibody:

a) having an association constant of at least about $1\times10^7$ molar$^{-1}$ with said DNA polymerase, b) being capable of inhibiting said DNA polymerase at a temperature $T_1$ which is less than about 85° C. such that the enzymatic activity of said DNA polymerase is inhibited, and said antibody being irreversibly inactivated at a temperature $T_2$ which is greater than $T_1$ and is also greater than about 40° C., so that said DNA polymerase regains its enzymatic activity, and c) being of either the IgM or IgG class.

15. The composition of claim 1 further comprising each of dATP, dCTP, dGTP and dTTP.

16. The composition of claim 1 further comprising more than one dNTP, a DNA polymerase cofactor, and a set of primers for polymerase chain reaction.

17. The composition of claim 1 which is buffered to a pH of from 7.5 to 9.5.

18. The composition of claim 1 wherein said thermostable DNA polymerase is present in an amount of at least 1 unit/100 µl, and said antibody is present in an amount of from 25 to 500 moles per mole of thermostable DNA polymerase.

* * * * *

UNITED STATES PATENT AND TRADEMARK OFFICE
CERTIFICATE OF CORRECTION

PATENT NO : 5,587,287
DATED : December 24, 1996
INVENTOR(S): Edward R. Scalice, et al.

It is certified that error appears in the above-identified patent and that said Letters Patent is hereby corrected as shown below:

Column 28, line 46, delete "$molar^{31\ 1}$" and insert -- $molar^{-1}$ --.

Signed and Sealed this

Twenty-sixth Day of August, 1997

Attest:

BRUCE LEHMAN

Attesting Officer

Commissioner of Patents and Trademarks

SEQUENCE LISTING ( 1 ) GENERAL INFORMATION ( i i i ) NUMBER OF SEQUENCES: 8

( 2 ) INFORMATION FOR SEQ ID NO:1:

( i ) SEQUENCE CHARACTERISTICS:
        ( A ) LENGTH: 28 nucleotides
        ( B ) TYPE: Nucleic acid
        ( C ) STRANDEDNESS: Single
        ( D ) TOPOLOGY: Linear ( i i ) MOLECULE TYPE: Primer ( i i i ) HYPOTHETICAL: No ( i v ) ANTI-SENSE: No ( v i ) ORIGINAL SOURCE: Synthetically prepared ( v i i ) IMMEDIATE SOURCE: Same ( x ) PUBLICATION INFORMATION: Known as SK38

( x i ) SEQUENCE DESCRIPTION: SEQ ID NO:1:

ATAATCCACC TATCCCAGTA GGAGAAAT         28

( 3 ) INFORMATION FOR SEQ ID NO:2:

( i ) SEQUENCE CHARACTERISTICS:
        ( A ) LENGTH: 28 nucleotides
        ( B ) TYPE: Nucleic acid
        ( C ) STRANDEDNESS: Single
        ( D ) TOPOLOGY: Linear ( i i ) MOLECULE TYPE: Primer ( i i i ) HYPOTHETICAL: No ( i v ) ANTI-SENSE: No ( v i ) ORIGINAL SOURCE: Synthetically prepared ( v i i ) IMMEDIATE SOURCE: Same ( x ) PUBLICATION INFORMATION: Known as SK39

( x i ) SEQUENCE DESCRIPTION: SEQ ID NO:2:

TTTGGTCCTT GTCTTATGTC CAGAATGC         28

( 4 ) INFORMATION FOR SEQ ID NO:3:

( i ) SEQUENCE CHARACTERISTICS:
        ( A ) LENGTH: 41 nucleotides
        ( B ) TYPE: Nucleic acid
        ( C ) STRANDEDNESS: Single
        ( D ) TOPOLOGY: Linear ( i i ) MOLECULE TYPE: Capture probe, HIV-I DNA ( i i i ) HYPOTHETICAL: No ( i v ) ANTI-SENSE: No ( v i ) ORIGINAL SOURCE: Synthetically prepared ( v i i ) IMMEDIATE SOURCE: Same ( x ) PUBLICATION INFORMATION: None ( x i ) SEQUENCE DESCRIPTION: SEQ ID NO:3:

ATCCTGGGAT TAAATAAAAT AGTAAGAATG TATAGCCCTA C                41

(5) INFORMATION FOR SEQ ID NO:4:

(i) SEQUENCE CHARACTERISTICS:
        (A) LENGTH: 31 nucleotides
        (B) TYPE: Nucleic acid
        (C) STRANDEDNESS: Single
        (D) TOPOLOGY: Linear (ii) MOLECULE TYPE: Probe, β-globin DNA (iii) HYPOTHETICAL: No (iv) ANTI-SENSE: No (vi) ORIGINAL SOURCE: Synthetically prepared (vii) IMMEDIATE SOURCE: Same (x) PUBLICATION INFORMATION: None (xi) SEQUENCE DESCRIPTION: SEQ ID NO:4:

CCTCAAACAG ACACCATGGT GCACCTGACT C                31

(6) INFORMATION FOR SEQ ID NO:5:

(i) SEQUENCE CHARACTERISTICS:
        (A) LENGTH: 28 nucleotides
        (B) TYPE: Nucleic acid
        (C) STRANDEDNESS: Single
        (D) TOPOLOGY: Linear (ii) MOLECULE TYPE: HIV-I DNA Primer (iii) HYPOTHETICAL: No (iv) ANTI-SENSE: No (vi) ORIGINAL SOURCE: Synthetically prepared (vii) IMMEDIATE SOURCE: Same (x) PUBLICATION INFORMATION: None (xi) SEQUENCE DESCRIPTION: SEQ ID NO:5:

AGTGGGGGGA CATCAAGCAG CCATGCAA                28

(7) INFORMATION FOR SEQ ID NO:6:

(i) SEQUENCE CHARACTERISTICS:
        (A) LENGTH: 28 nucleotides
        (B) TYPE: Nucleic acid
        (C) STRANDEDNESS: Single
        (D) TOPOLOGY: Linear (ii) MOLECULE TYPE: HIV-I DNA Primer (iii) HYPOTHETICAL: No (iv) ANTI-SENSE: No (vi) ORIGINAL SOURCE: Synthetically prepared (vii) IMMEDIATE SOURCE: Same (x) PUBLICATION INFORMATION: None (xi) SEQUENCE DESCRIPTION: SEQ ID NO:6:

TTCCTGCTAT GTCACTTCCC CTTGGTTC                28

(8) INFORMATION FOR SEQ ID NO:7:

(i) SEQUENCE CHARACTERISTICS:
    (A) LENGTH: 28 nucleotides
    (B) TYPE: Nucleic acid
    (C) STRANDEDNESS: Single
    (D) TOPOLOGY: Linear (ii) MOLECULE TYPE: HIV-I DNA Primer (iii) HYPOTHETICAL: No (iv) ANTI-SENSE: No (vi) ORIGINAL SOURCE: Synthetically prepared (vii) IMMEDIATE SOURCE: Same (x) PUBLICATION INFORMATION: None (xi) SEQUENCE DESCRIPTION: SEQ ID NO:7:

TAGCACCCAC CAGGGCAAAG AGAAGAGT                                              28

(9) INFORMATION FOR SEQ ID NO:8:

(i) SEQUENCE CHARACTERISTICS:
    (A) LENGTH: 28 nucleotides
    (B) TYPE: Nucleic acid
    (C) STRANDEDNESS: Single
    (D) TOPOLOGY: Linear (ii) MOLECULE TYPE: HIV-I DNA Primer (iii) HYPOTHETICAL: No (iv) ANTI-SENSE: No (vi) ORIGINAL SOURCE: Synthetically prepared (vii) IMMEDIATE SOURCE: Same (x) PUBLICATION INFORMATION: None (xi) SEQUENCE DESCRIPTION: SEQ ID NO:8:

AGATGCTGTT GCGCCTCAAT AGCCCTCA                                              28